(12) United States Patent  (10) Patent No.: US 7,535,009 B2
Juestel et al.  (45) Date of Patent: May 19, 2009

(54) DEVICE FOR GENERATING IMAGES AND/OR PROJECTIONS

(75) Inventors: Thomas Juestel, Aachen (DE); Walter Mayr, Alsdorf (DE); Herfried Karl Wieczorek, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 185 days.

(21) Appl. No.: 10/524,959

(22) PCT Filed: Aug. 14, 2003

(86) PCT No.: PCT/IB03/03614

§ 371 (c)(1),
(2), (4) Date: Jul. 22, 2005

(87) PCT Pub. No.: WO2004/019059

PCT Pub. Date: Mar. 4, 2004

(65) Prior Publication Data

US 2006/0000977 A1    Jan. 5, 2006

(30) Foreign Application Priority Data

Aug. 22, 2002  (DE) ................. 102 38 398

(51) Int. Cl.
*G01T 1/20* (2006.01)
(52) U.S. Cl. ............................. 250/367
(58) Field of Classification Search .......... 250/367
See application file for complete search history.

(56) References Cited

U.S. PATENT DOCUMENTS

| 4,499,159 A | | 2/1985 | Brines et al. |
| 5,273,681 A | * | 12/1993 | Srivastava ............ 252/301.4 R |
| 5,334,839 A | * | 8/1994 | Anderson et al. ........... 250/368 |
| 5,640,016 A | | 6/1997 | Matsuda et al. |
| 5,909,029 A | * | 6/1999 | Tonami et al. .............. 250/367 |
| 6,278,832 B1 | * | 8/2001 | Zagumennyi et al. ....... 385/141 |
| 6,689,293 B2 | * | 2/2004 | McClellan et al. .... 252/301.4 F |
| 6,734,631 B2 | * | 5/2004 | Juestel et al. ............... 313/640 |
| 2001/0006214 A1 | | 7/2001 | Boerner et al. |
| 2001/0028700 A1 | | 10/2001 | Duclos et al. |
| 2001/0033133 A1 | | 10/2001 | Justel et al. |
| 2006/0027742 A1 | * | 2/2006 | Srivastava et al. .......... 250/256 |

FOREIGN PATENT DOCUMENTS

| EP | 1 004 899 A1 | 5/2000 |
| JP | 2000-235078 | 8/2000 |

OTHER PUBLICATIONS

Dorenbos, et al.; Scintillation properties of some Ce+ and Pr+ doped inorganic crystals; 1993, IEEE, pp. 281-283.
Horchani, et al.; Scintillation poperties of CsPrP4O12 and RbPrP4O12; 2002; Nuclear Instruments & Methods in Physics Research; 486:283-287.
Van Eijk, et al.; Nd3 and Pr3 Doped Inorganic Scintillators; 1994; IEEE; pp. 664-667.
Zhang, et al.; Elaboration and Spectroscopic Properties of Orthoborates YBo3 and LuBO3 and Lu4Al2O9 Crystalline Solid; Electro. Society Proc.; 97-29:pp. 342-351.

* cited by examiner

*Primary Examiner*—David P Porta
*Assistant Examiner*—Jessica L Eley

(57) ABSTRACT

The invention relates to a device for generating images and/or projections, which device includes a device for the detection of input radiation. The device for the detection of input radiation comprises a sensor with a $Pr^{3+}$-activated scintillator for converting the input radiation into UV radiation. The $Pr^{3+}$-activated scintillators have short excitation and decay times.

19 Claims, 4 Drawing Sheets

DEVICE FOR GENERATING IMAGES AND/OR PROJECTIONS

Figure 1:
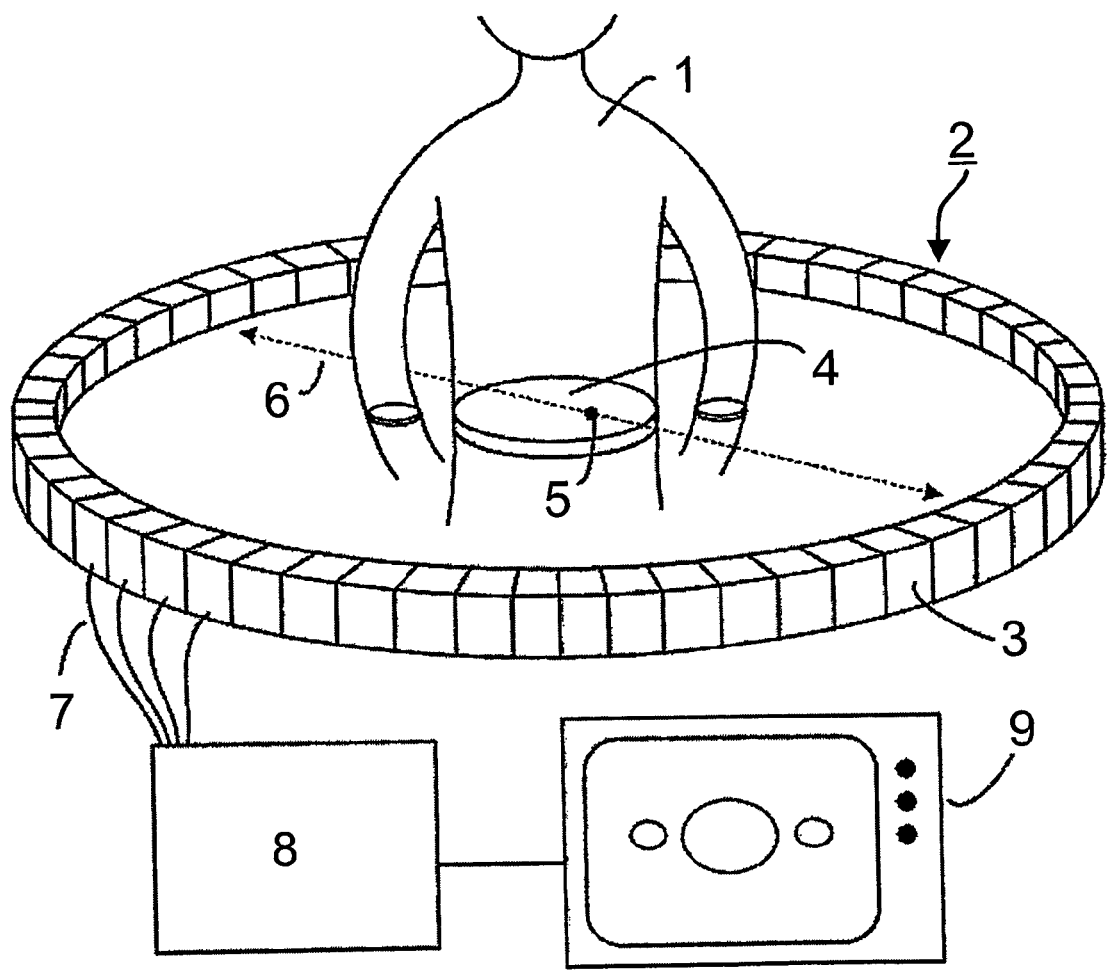

The invention relates to a device for generating images and/or projections by means of an imaging method, which device includes a device for the detection of input radiation which includes at least one acquisition element which comprises a sensor for converting the input radiation and a photodiode which converts an optical signal into an electrical signal. The invention also relates to a device for the detection of input radiation.

Tomography is a slice imaging method used in the field of medical X-ray diagnosis. According to this method a coupled motion of the tube and the film takes place in opposite directions while the patient remains stationary. A given, selected depth zone is thus sharply imaged on the film, whereas parts of the objects which are situated higher or deeper are blurred because of the continuously changing projection.

In X-ray tomography the attenuation of X-rays by a given slice of the body of the patient is measured by means of a plurality of detectors in different projection directions. To this end, a narrow X-ray beam (fan beam) is formed by means of an X-ray tube and diaphragms. This beam traverses the relevant part of the body and is attenuated to a different degree by the various structures within the body (for example, the skin, fat, muscles, organs, bones).

Exactly opposite the X-ray tube there is arranged a plurality of detectors which receive the attenuated signal and process it electronically so as to propagate it to a computer for evaluation. Subsequently, the X-ray tube and the oppositely situated detectors are rotated slightly further around the patient.

The described procedure is then repeated. Various views (projections) of the same slice are thus generated and converted into a grey scale image in the computer. This image can be viewed and evaluated on a display screen or an X-ray film. This technique yields images which contain significantly more contrast than those produced by a conventional X-ray technique.

A further method based on the principle of tomography is called Emission Computer Tomography (ECT) which is based on the measurement in slices of temporarily incorporated radionuclides (scintigraphy). The emission of positrons from $^{15}O$ carbon dioxide or $^{68}Ge$ (Positron Emission Computer Tomography or PET) or photons from $^{99m}Tc$ or $^{123}I$ (Single Photon Emission Computer Tomography or SPECT) is then measured. Such nuclear medical tomography methods offer the advantage that they present the viewer of the tomographically generated image with information which goes beyond pure morphology and which possibly also images physiological events.

In contemporary computer tomography two basic types of radiation detectors can be distinguished: direct converters (for example, xenon gas detectors) and scintillation detectors. In the case of solid-state detectors, made of a scintillation material (scintillator), the visible light emitted after excitation is collected by photodiodes. In X-ray computer tomography solid-state detectors contain either cadmium tungstate ($CdWO_4$) or materials on the basis of rare earths. Frequently used scintillators are $Ce^{3+}$-doped materials such as, for example, $Lu_2SiO_5$:Ce or $Gd_2SiO_5$:Ce. In PET methods or in SPECT methods the scintillator often used is NaI:Tl or bismuth germanate-$Bi_4Ge_3O_{12}$ (BGO). Detectors provided with a scintillator in the form of $Ce^{3+}$-doped materials are known, for example, from EP 1 004 899.

The scintillator must satisfy some conditions. For example, the scintillator must have a high density, a high luminous efficiency and a short excitation and decay time.

The decay time $\tau$ of NaI:Tl amounts to 250 ns, that of BGO to 300 ns, that of $Lu_2SiO_5$:Ce to 40 ns and that of $Gd_2SiO_5$:Ce to 56 ns. For many applications it is desirable to utilize scintillators having even shorter decay times.

Therefore, it is an object of the invention to provide a device for tomography which comprises a scintillator having a shorter decay time $\tau$.

This object is achieved by means of a device for generating images and/or projections by means of an imaging method, which device includes a device for the detection of input radiation which includes at least one acquisition element which comprises a sensor with a $Pr^{3+}$-activated scintillator for converting the input radiation into UV radiation and a photodiode which converts an optical signal into an electrical signal.

$Pr^{3+}$-activated scintillators have short decay times $\tau$ in the range below 25 ns which, therefore, are even shorter than those of $Ce^{3+}$-activated scintillators.

Because of the short decay time $\tau$, the integration time can be reduced during the determination of the intensity of the input radiation, so that the image rate for the generating of images and/or projections can be significantly increased. Because of the increased image rate, the occurrence of artifacts, for example, shadow images, is reduced. Furthermore, the examination time is reduced for the patient, because more single images can be measured within a shorter period of time.

The advantageously selected $Pr^{3+}$-activated scintillators in conformity with claim 2 have short excitation times and short decay times $\tau$. Furthermore, they emit UV radiation in response to excitation by means of X-rays or γ quanta.

For the advantageously chosen imaging methods in conformity with the claims 3 to 5 it is important that the scintillator has a short decay time and hence enables a high image rate. The time window is of major importance notably for the PET method and it is particularly advantageous to utilize a scintillator having a short decay time in the device for determining input radiation.

The advantageous embodiments in conformity with the claims 6 to 8 make it possible to use a larger part of the input radiation for the image analysis. The luminous substance that can be excited by ultraviolet radiation absorbs the ultraviolet radiation emitted by the scintillator and converts it into long-wave radiation adapted to the spectral sensitivity of the photodiode. As a result, overlapping of the emission spectrum of the scintillator and the sensitivity spectrum of the photodiode is maximum and the photodiode can operate with a maximum quantum efficiency.

The invention also relates to a device for the detection of input radiation which includes at least one acquisition element which comprises a sensor with a $Pr^{3+}$-activated scintillator for converting the input radiation into ultraviolet radiation and a photodiode which converts an optical signal into an electrical signal.

Figure 2:
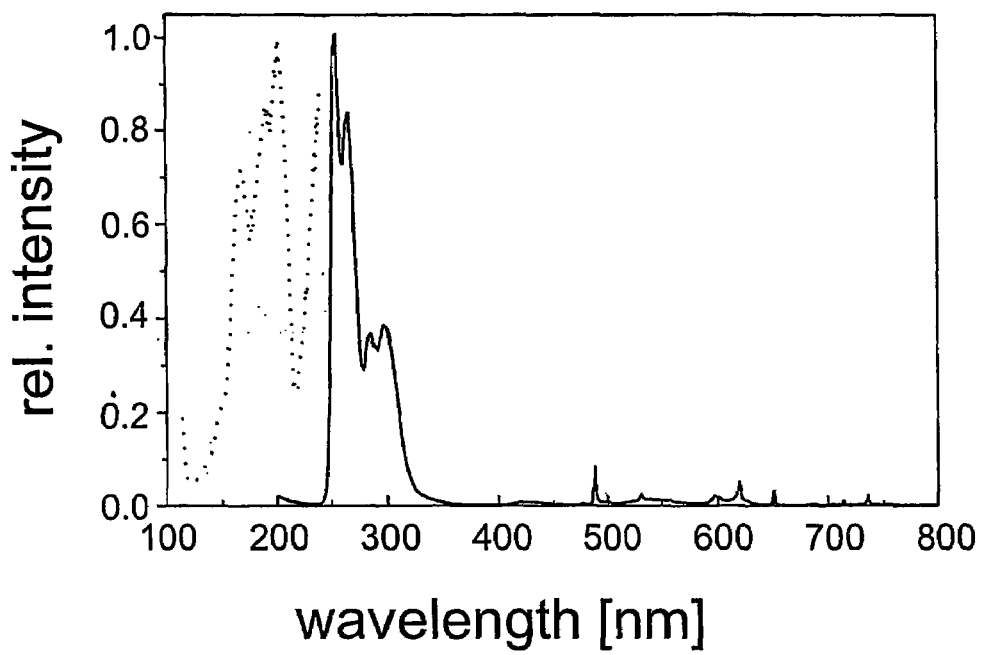
Figure 3:
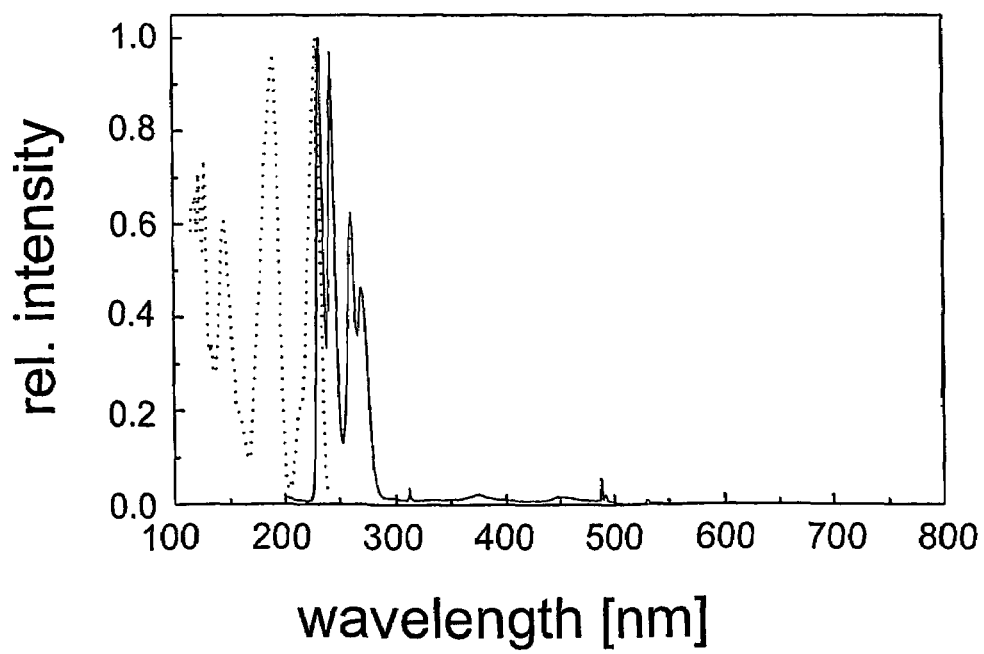
Figure 4:
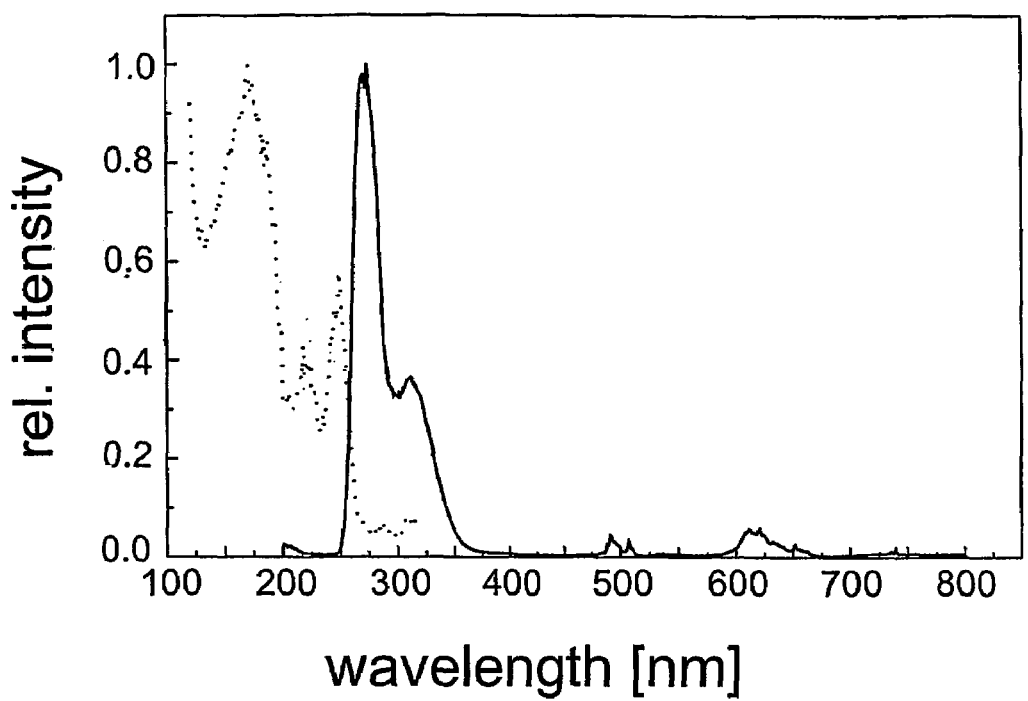
Figure 5:
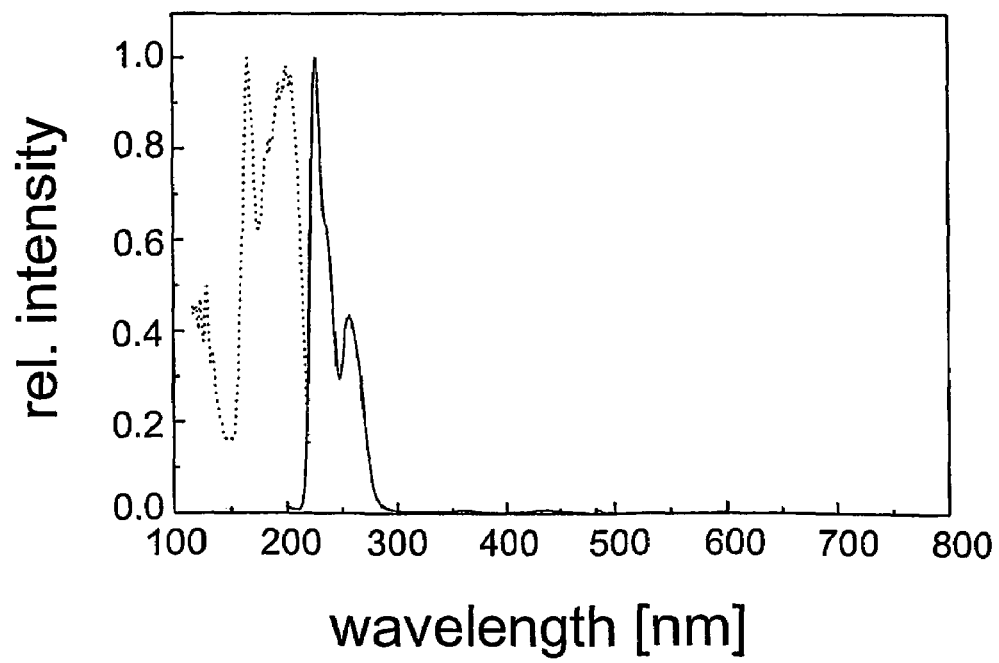

Embodiments of the invention will be described in detail hereinafter with reference to the accompanying Figures. Therein:

FIG. 1 is a diagrammatic representation of the construction of a device for generating images and/or projections by means of the PET method, FIG. 2 shows the excitation and emission spectrum of $CaLi_2SiO_4$:Pr, Na, FIG. 3 shows the excitation and emission spectrum of $LuPO_4$:Pr, FIG. 4 shows the excitation and emission spectrum of $Lu_2SiO_5$:Pr, and FIG. 5 shows the excitation and emission spectrum of $LaPO_4$:Pr.

Figure 6:
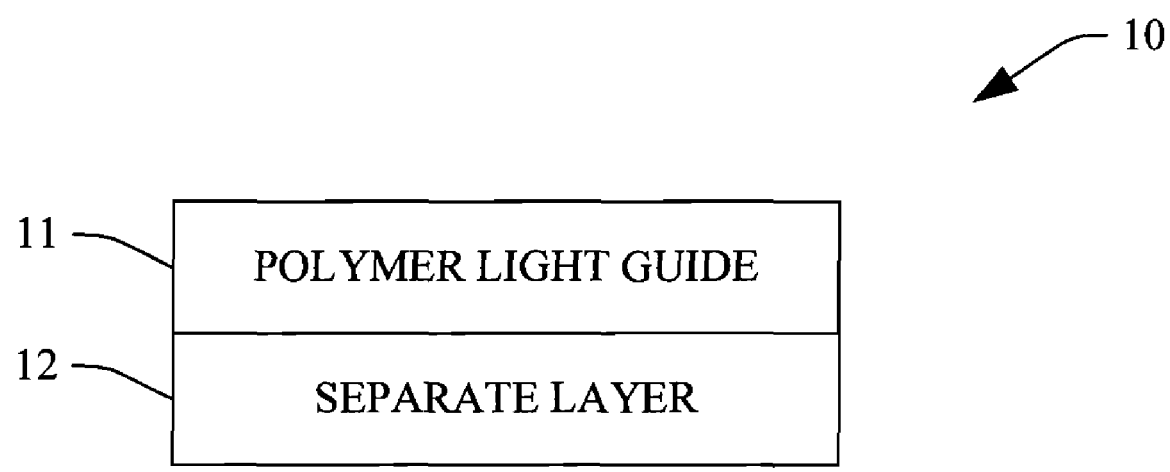

FIG. 6 shows a color converter that includes a polymer light guide and a separate layer.

A device for generating images and/or projections can operate with various imaging methods. Preferably, the device is arranged to carry out the PET method or the SPECT method as the imaging method, or to carry out the imaging method by means of X-rays.

In conformity with the PET method, a metabolic preparation marked with given, unstable nuclides is injected into a patient; this preparation is taken up in a tissue-specific or function-specific manner. The radionuclides used decay, giving rise to two γ quanta in different successive processes in the vicinity of the location of decay; these two quanta fly in exactly opposite directions and leave the patient so as to be detected by the sensors which are arranged in the form of a ring around the patient in the device for the detection of input radiation. During their travel from the location of origin to the location where they emerge from the patient the γ quanta traverse further tissue of the patient; this tissue can absorb the γ quanta more or less in dependence on the type of tissue. Generally speaking, the γ quanta are attenuated in a tissue-specific manner. All detected γ quanta together form a set of projections of the image wherefrom a slice image or volume image is reconstructed in known manner during a subsequent reconstruction operation. The PET method yields functional images of the object.

The two γ quanta have the same energy of 511 keV. The detection of the γ quanta is performed by means of scintillators in the sensor of the device for the detection of input radiation.

FIG. 1 is a diagrammatic representation of a device for forming a slice image by means of the PET method. The patient, or the object to be examined 1, is arranged within a ring-like device 2 for the detection of input radiation which consists of individual detection or acquisition elements 3. The plane defined by the ring intersects the object 1, for example, in the plane of intersection 4. The described decay process takes place at the location 5 where two γ quanta leave the object 1 in opposite directions along the double arrow 6. The individual sensor elements 3 of the device 2 for the detection of input radiation are connected, via leads 7, to a data processing unit 8 which evaluates the signals from the detection elements 3. The slice image formed is subsequently displayed on a display device 8.

A high temporal resolution is very important for the PET method, because the entire process from the emission of the positron until the detection of the γ quanta takes place within a few nanoseconds. Because of the short decay time τ, the integration time during the determination of the intensity of the input radiation can be reduced, so that the image rate can be significantly increased. As a result of the increased image rate, a higher dose of nuclides can be administered to the patient so as to reduce the overall examination time.

Furthermore, for the PET method it is also important to determine the energy of the γ quanta in order to ensure that they have not left their original trajectory due to scattering processes. Such γ quanta have an energy value which is lower than 511 keV. The energy value of the γ quanta is determined from the level of the detected signal. In this respect it is important that the scintillator is in the normal state again and not in an excited state still, as otherwise an energy value of 511 keV will be unduly determined, despite the fact that the γ quantum was scattered and has a lower energy value.

The SPECT method also is a nuclear medical examination method. The nuclides used for the SPECT method originate from natural decay and emitted γ quanta with energies of 141 keV ($^{99m}$Tc) at 159 keV ($^{123}$I). Like in the PET method, the emitted γ quanta are detected by the device for the detection of input radiation and their signal is amplified. However, a collimator is arranged in front of each detection element. The collimator serves as an objective and consists of a lead plate which is provided with bores which are arranged in parallel or in a converging fashion. γ quanta which are incident at an angle are absorbed by the collimator, thus enabling the three-dimensional imaging.

In the case of X-ray computer-tomography the device for generating images or projections includes an X-ray tube which emits a fine, usually fan-shaped beam and moves in a circle around the longitudinal axis of the object to be examined. After having traversed the object, the X-rays transmitted by the tissue of the object are captured again by an oppositely situated device for the detection of input radiation. For small fields of a format of approximately 1.5×1.5 mm the computer calculates the difference between the emitted energy and the received intensity of the X-ray beam and forms from the different values a grey scale image which is displayed on a display device. The grey values correspond to the respective relative density of the tissue.

Like in the PET method, according to the latter two methods the integration time during the detection of the intensity of the input radiation can again be reduced as a result of the short decay time τ, so that the image rate for the generating of images and/or projections can be significantly increased. As a result of the increased image rate, the occurrence of artifacts, such as shadow images, is reduced and also the period of time required to carry out the imaging method.

The device for the detection of input radiation may be composed of a plurality of acquisition elements, each acquisition element comprising a sensor for converting the input radiation into UV radiation and a photodiode. It is particularly advantageous when each acquisition element comprises an array of photodiodes. The sensor and the photodiode array are customarily formed as a respective layer and combined so as to form a system of layers.

The sensor layer constitutes the entrance screen for the input radiation which is preferably formed by X-rays or γ rays. Underneath the sensor layer there is arranged the layer with the photodiodes. Electrical contact leads extend from the layer with the photodiodes to the electronic read-out circuitry.

The essential element of the sensor is formed by a layer of a $Pr^{3+}$-activated scintillator which converts the input radiation into UV radiation. It is very advantageous when the sensor comprises a layer of $LaPO_4$:Pr, $LuF_3$:Pr, $LuCl_3$:Pr, $LuBr_3$:Pr, $(Lu_{1-x}Y_x)$:Pr, where $0 \leq x \leq 1$, $(Lu_{2-x}Y_x)SiO_5$:Pr, where $0 \leq x \leq 1$, $(Lu_{1-x}Y_x)Si_2O_7$:Pr, where $0 \leq x \leq 1$, $(Lu_{1-x}Y_x)BO_3$:Pr, where $0 \leq x \leq 1$, :$Pr_yNa_y$, where $0.001 \leq y \leq 0.2$. Such $Pr^{3+}$-activated materials emit UV radiation after excitation and have short decay times.

TABLE 1

Emission bands and decay times of selected $Pr^{3+}$-activated and $Ce^{3+}$-activated scintillators.

| Scintillator | Emission wavelength $\lambda_{max}$ [nm] | Decay time τ [ns] |
|---|---|---|
| $LuPO_4$:Pr | 235 | 9 |
| $Lu_2SiO_5$:Pr | 270 | 16 |
| $LuPO_4$:Ce | 350 | 24 |
| $Lu_2SiO_5$:Ce | 420 | 40 |

The shorter decay time τ of the $Pr^{3+}$-activated scintillators, that is, in comparison with the corresponding $Ce^{3+}$-activated scintillators, can be derived from the ratio $\tau \approx 1/\lambda_{max}^2$. The 5d levels of the free $Pr^{3+}$ cation are situated approximately 62000 $cm^{-1}$ above the 4f levels, whereas this energy difference amounts to only 50000 $cm^{-1}$ in the free $Ce^{3+}$ cation. This larger energy difference is also responsible for the fact that the emission bands of $Pr^{3+}$-activated scintillators, originating from 5d-4f transitions, are of higher energy than the emission bands of corresponding $Ce^{3+}$-activated scintillators. Therefore, their main emission bands of the $Pr^{3+}$-activated scintillators in accordance with the invention are situated in the range from 220 to 350 nm, so in the range of UV radiation, whereas the emission bands of $Ce^{3+}$-activated scintillators are of a significantly longer wavelength.

The sensor layer with the $Pr^{3+}$-activated scintillator is customarily formed by pressing. A powder of the appropriate $Pr^{3+}$-activated scintillator is formed first; this powder is subsequently converted into a crystal layer by means of a pressing method, for example, high-pressure cold pressing or high-temperature isostatic pressing. The size of such pressed crystals is in the range of from a few millimeters to a few centimeters. A sensor layer of this kind is bonded to the layer with the photodiodes.

The powdery scintillator material can be formed from the starting compounds by a solid-state reaction as well as by reactions in an aqueous or aqueous-alcoholic solution. During the latter reaction the relevant metal salts and/or metal oxides are possibly dissolved or suspended with a combination of the anion of the scintillator in water or a water-alcohol mixture so as to be reacted.

In the photodiodes the UV radiation is converted into electrical signals. Because of the emission in the range of UV radiation, only UV-sensitive photodiodes can be used in the device for the detection of input radiation. For example, photodiodes with $Cs_3Sb$ photocathodes, bialkaline photocathodes or multialkaline photocathodes can be used. Furthermore, use can also be made of photodiodes based on Si, GaN or AlGaN.

In order to enlarge the choice of suitable photodiodes, a color converter 10 which converts UV radiation into radiation of longer wavelength can be arranged between the sensor layer and the layer with the photodiodes. To this end, the color converter 10 contains a luminous substance which can be excited by UV radiation. The color converter 10 thus converts the UV radiation emitted by the sensor into radiation having a wavelength range which corresponds to the maximum of the spectral sensitivity of the photodiode used. The radiation of longer wavelength may comprise colored light or infrared radiation.

For the luminous substances use can notably be made of organic luminous substances with a high photoluminescence quantum efficiency and a short decay time τ. Particularly attractive luminous substances are Coumarins such as Coumarin 1 ($\lambda_{max}$=430 nm) or Courmarin 120 ($\alpha_{max}$=442 nm) or Lumogen dyes such as Lumogen F Violet 570 marketed by BASF. The decay times τ of these luminous substances are less than 10 ns.

Turning briefly to FIG. 6, the color converter 10 may comprise, for example, a polymer light guide 11 which is doped with the luminous substance. The polymer light guide 11 may contain, for example, polymethylmethacrylate, polystyrol, polytetrafluoroethylene, polycarbonate, polyimide or polyvinylchloride. Alternatively, the color converter 10 may comprise two components, that is, the polymer light guide 11 and a separate layer 12 with the luminous substance. In this embodiment the polymer light guide 11 adjoins the sensor layer of the acquisition element; the separate layer 12 with the luminous substance adjoins the polymer light guide 11 and is adjoined itself by the layer with the photodiodes.

EXAMPLE 1

For the production of $Ca_{0.98}Li_2SiO_4:Pr_{0.01},Na_{0.01}$, 25.0 g (278 mmol) $Li_2SiO_3$, 147 mg (1.39 mmol) $Na_2CO_3$, 27.3 g (272 mmol) $CaCO_3$ and 1.21 g (2.78 mmol) $Pr(NO_3)_3 \cdot 6H_2O$ were mixed in demineralized $H_2O$ and suspended. The water was removed by distillation and the residue obtained was dried. Subsequently, the reaction product was annealed once in air at 700° C. for two hours and annealed twice in a CO atmosphere at 850° C. for each time 12 hours. The scintillator powder was rinsed several times with water and ethanol, dried and ground on a roller device for several hours. The resultant scintillator powder had an average particle size of 3 μm. The excitation and emission spectrum of this scintillator is shown in FIG. 2. The decay time τ of $Ca_{0.98}Li_2SiO_4:Pr_{0.01},Na_{0.01}$ amounts to 16 ns.

EXAMPLE 2

40.0 g (101 mmol) $Lu_2O_3$ and 883 mg (2.03 mmol) $Pr(NO_3)_3 \cdot 6H_2O$ were suspended in 200 ml ethanol in order to produce $LuPO_4$:Pr. 25.8 g (223 mmol) 85% phosphoric acid was added slowly while stirring. The suspension was stirred for twenty-four hours and subsequently concentrated in a rotary evaporator. The residue was dried at 100° C., mortarized and mixed with 500 mg $NH_4Cl$. Subsequently, the scintillator powder was calcinated twice for 2 hours at 1250° C. in a CO atmosphere and subsequently mortarized each time again. Finally, the scintillator powder was calcinated once more in air at 1250° C. for 1 hour. The excitation and emission spectrum of this scintillator is shown in FIG. 3. The decay time c of $LuPO_4$:Pr amounts to 9 ns.

EXAMPLE 3

10.0 g (25.1 mmol) $Lu_2O_3$, 1.51 g (25.1 mmol) and 86.0 mg (84.1 μmol) $Pr_6O_{11}$ were suspended in 200 ml ethanol in order to produce $Lu_2SiO_5$:Pr. The suspension was treated in an ultrasound bath for ten minutes and subsequently concentrated in a rotary evaporator. The residue obtained was dried at 100° C., mortarized and mixed with 500 mg CsF. Subsequently, calcination took place in a CO atmosphere for 6 hours at 1350° C. and the scintillator powder obtained was subsequently mortarized. Finally, the scintillator powder was rinsed in 500 ml water for two hours, sucked off and dried at 100° C. The excitation and emission spectrum of this scintillator is shown in FIG. 5. The decay time τ of $Lu_2SiO_5$:Pr amounts to 16 ns.

EXAMPLE 4

91.4 g (282 mmol) $La_2O_3$ and 883 mg (2.48 mmol) $PrCl_3 \cdot 6H_2O$ were suspended in 200 ml water in order to manufacture $LaPO_4$:Pr. 69.0 g (598 mmol) 85% phosphoric acid was added slowly while stirring. The suspension was stirred for 24 hours and subsequently concentrated in a rotary evaporator. The residue obtained was dried at 100° C., mortarized and mixed with 1.2 g LiF. The scintillator was calcinated in a nitrogen atmosphere for 2 hours at 1000° C. The scintillator powder obtained was rinsed in diluted $HNO_3$ for 6 hours at 60° C. Finally, the scintillator was sucked off, rinsed acid free with water and dried at 100° C. FIG. 6 shows the excitation and emission spectrum of this scintillator. The decay time τ of LaPO$_4$:Pr amounts to 11 ns.

The invention claimed is:

1. A device for generating images and/or projections by means of an imaging method, which device includes a device for the detection of input radiation which includes at least one acquisition element which comprises a sensor with a Pr$^{3+}$-activated scintillator for converting the input radiation into UV radiation, a color converter which contains a luminous substance for converting the UV radiation to an optical signal, and a photodiode which converts an optical signal into an electrical signal; wherein the Pr$^{3+}$-activated scintillator is chosen from the group LuF$_3$: Pr, LuCl$_3$:Pr, and LuBr$_3$:Pr.

2. A device for generating images and/or projections as claimed in claim 1, wherein the device is arranged to carry out the PET method as the imaging method.

3. A device for generating images and/or projections as claimed in claim 1, wherein the device is arranged to carry out the SPECT method as the imaging method.

4. A device for generating images and/or projections as claimed in claim 1, wherein the device is arranged to carry out the imaging method by means of X-rays.

5. A device for generating images and/or projections as claimed in claim 1, wherein the color converter comprises a polymer light guide which is doped with the luminous substance that is excited by UV radiation.

6. A device for generating images and/or projections as claimed in claim 1, wherein the color converter comprises a polymer light guide and a separate layer with the luminous substance that is excited by UV radiation.

7. A device for generating images and/or projections as claimed in claim 1, wherein the luminous substance includes an organic material.

8. A device for the detection of input radiation which includes at least one acquisition element which comprises a sensor with a Pr$^{3+}$-activated scintillator for converting the input radiation into UV radiation, a color converter that converts UV radiation to an optical signal, and a photodiode which converts the optical signal into an electrical signal, wherein the color converter includes a polymer light guide and the color converter is doped with a Courmarin based substance.

9. A device for detecting input radiation as claimed in claim 8, wherein the color converter contains a luminous substance which can be excited by UV radiation, wherein the color converter is arranged between the sensor and the photodiode.

10. A device for detecting input radiation as claimed in claim 8, wherein the acquisition element comprises an array of photodiodes, and further wherein the array of photodiodes forms a first layer and the sensor forms a second layer, wherein the first and second layers are combined to form a system of layers.

11. A device for detecting input radiation as claimed in claim 8, wherein a decay time of the scintillator is approximately 9 ns.

12. A device for detecting input radiation as claimed in claim 8, wherein a decay time of the scintillator is approximately 16 ns.

13. A device for detecting input radiation as claimed in claim 8, wherein the Pr$^{3+}$-activated scintillator is Ca$_{1-2y}$Li$_2$SiO$_4$:Pr$_y$Na$_y$, where $0.001 \leq y \leq 0.2$.

14. A device for detecting input radiation as claimed in claim 8, wherein the Pr$^{3+}$-activated scintillator is LaPO$_4$:Pr.

15. A device for detecting input radiation as claimed in claim 8, wherein the Pr$^{3+}$-activated scintillator is one of LuCl$_3$:Pr, LuBr$_3$:Pr, (Lu$_{2-x}$Y$_x$)SiO$_5$:Pr, where $0 \leq x \leq 1$, and (Lu$_{1-x}$Y$_x$)Si$_2$O$_7$:Pr, where $0 \leq x \leq 1$.

16. An imaging method, comprising:
receiving one of an X-ray and a γ quantum at a Pr$^{3+}$-activated scintillator, wherein the Pr$^{3+}$-activated scintillator is one of LuCl$_3$:Pr, LuBr$_3$:Pr;
receiving UV radiation emitted form the scintillator at a color converter in response to receipt of the one of the XC-ray and the γ quantum;
receiving a light signal emitted from the color converter at a photodiode;
generating an electrical signal in response to receipt of the light signal; and
generating an image based at least in part upon the generated electrical signal.

17. The imaging method of claim 16, wherein the color converter includes a polymer light guide that is doped with a luminous substance.

18. The imaging method of claim 16, wherein the color converter includes a polymer light guide and a separate layer with a luminous substance.

19. The device for detecting input radiation as claimed in claim 16, wherein the color convener is doped with a Courmarin based substance.

* * * * *